United States Patent [19]

Dinizo

[11] Patent Number: 4,886,936
[45] Date of Patent: Dec. 12, 1989

[54] PROCESS FOR THE PRODUCTION OF ORTHO-NITROBENZONITRILES

[75] Inventor: Stephen E. Dinizo, San Lorenzo, Calif.

[73] Assignee: ICI Americas Inc., Wilmington, Del.

[21] Appl. No.: 231,921

[22] Filed: Aug. 15, 1988

[51] Int. Cl.$^4$ .......................................... C07C 121/78
[52] U.S. Cl. .................................................... 558/343
[58] Field of Search .......................................... 558/343

[56] References Cited

U.S. PATENT DOCUMENTS

| | | | |
|---|---|---|---|
| 1,702,711 | 2/1929 | Trusler | 558/343 |
| 2,195,076 | 3/1940 | Braun et al. | 260/465 |
| 4,677,219 | 6/1987 | Berman et al. | 558/418 |

FOREIGN PATENT DOCUMENTS 0047830  10/1986  Japan .................................. 558/343

*Primary Examiner*—Mary C. Lee
*Assistant Examiner*—Zinna Northington-Davis
*Attorney, Agent, or Firm*—Joel G. Ackerman

[57] ABSTRACT

Ortho-nitrobenzonitriles are produced from the corresponding ortho-nitrochlorobenzenes by reaction with cuprous cyanide and an alkali metal bromide, an alkaline earth metal bromide, or zinc bromide or with a combination of lithium cyanide and cuprous bromide, optionally in the presence of a solvent.

9 Claims, No Drawings

PROCESS FOR THE PRODUCTION OF ORTHO-NITROBENZONITRILES

BACKGROUND AND PRIOR ART OF THE INVENTION

This invention relates to an improved process for production of ortho-nitrobenzonitriles. Compounds of this type have the general formula

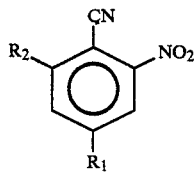

in which $R_1$ and $R_2$ independently represent hydrogen or various electron-withdrawing groups such as nitro, cyano, halomethyl (particularly trihalomethyl), lower alkylsulfonyl, and halo-(lower alkyl)sulfonyl.

Various processes are known for the production of compounds of this type including the general process of cyanation of a similarly substituted halobenzene.

One such process is described in U.S. Pat. No. 2,195,076. That process uses a combination of cuprous cyanide and a compound capable of forming a "double compound" with the cuprous cynaide, particularly certain nitrogenous bases. The patent states that in many cases it is preferable to add inorganic salts, preferably copper salts, or also halides of alkali metals, aluminum, zinc, mercury or iron. This patent contains a total of 33 examples describing production of various compounds by the general process. One of the compounds prepared, in Example 18, is 4-cyano-3-nitro-1-trifluoromethylbenzene. In that example the compound is produced using a combination of cuprous cyanide, cuprous chloride and quinoline. An attempt was made to repeat this example to determine the yield of the product, as the example did not provide such information. However, little or no desired product was observed, with tarry products predominating. Lowering of the temperature did not result in any significant improvement.

Most of the examples of U.S. Pat. No. 2,195,076 show the use of cuprous cyanide alone or in combination with another copper salt, usually cuprous chloride or bromide. The only salt of any other metal which is disclosed in an example used in combination with cuprous cyanide, is sodium cyanide.

Japanese Patent Application 60/47830 (publication number) of Nippon Kayaku Company discloses a method for producing ortho-nitrobenzonitrile compounds employing an alkali metal cyanide, cuprous chloride (or cuprous chloride plus a cupric salt) and a polar aprotic or basic solvent.

SUMMARY OF THE INVENTION

The present invention comprises a process for production of an ortho-nitrobenzonitrile by reaction of the corresponding ortho-nitrochlorobenzene with: (a) cuprous cyanide and a metal bromide selected from alkali metal bromides, alkaline earth metal bromides and zinc bromide, or (b) cuprous bromide and lithium cyanide, at a temperature of from about 100° to about 200° C., optionally in the presence of a solvent.

DETAILED DESCRIPTION OF THE INVENTION

Compounds produced by the process of this invention can be characterized by the general formula

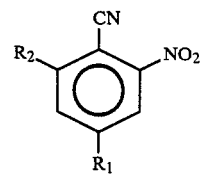

in which $R_1$ and $R_2$ are independently hydrogen or electron-withdrawing groups. Examples of such electron-withdrawing groups are nitro, $C_1$–$C_4$ alkylsulfonyl (such as methylsulfonyl, ethylsulfonyl, n-propylsulfonyl, etc.), halo-($C_1$–$C_4$ alkyl)sulfonyl (for instance, chloromethylsulfonyl), cyano, carboxyl and halomethyl (particularly trihalomethyl such as trifluoromethyl and trichloromethyl).

Some compounds of this class are:
ortho-nitrobenzonitrile,
2,6-dinitrobenzonitrile,
4-cyano-3-nitro-benzotrifluoride,
4-cyano-3-nitro-benzotrichloride,
2-nitro-4-methylsulfonylbenzonitrile,
4-cyano-3-nitrobenzoic acid, and
2,5-dicyanonitrobenzene.

Such compounds can be advantageously obtained by reaction of the corresponding chlorobenzene with cuprous cyanide and an alkali metal bromide, an alkaline earth metal bromide or zinc bromide, or alternatively with a combination of cuprous bromide and lithium cyanide, without the need for a "double salt compound" of copper as in U.S. Pat. No. 2,195,076.

When cuprous cyanide is employed, it is preferably used in an approximately stoichiometric amount with respect to the starting chlorobenzene. The metal bromide employed together with the cuprous cyanide is used in an amount of from about 0.1 to about 2.0, preferably from about 0.5 to about 1.0 equivalents, with respect to the chlorobenzene.

In addition to the metal bromide, there may be used a second bromie-containing substance such as tetraphenylphosphonium bromide or cupric bromide. If a second such bromine-containing substance is used, it is generally used in a minor amount, preferably about 0.1 equivalent with respect to the starting chlorobenzene.

Reaction temperatures generally range from about 100° to about 200° C., preferably from about 150° to about 200° C. Reaction times may be as short as 3 hours for complete or near complete reaction, depending on the starting material, the temperature and the bromide.

The reaction may be conducted without a solvent. However, if a solvent is not used longer reaction times generally will be necessary for more complete reaction in the above temperature range. Consequently, the reaction is preferably conducted in the presence of a solvent, most preferably a nitrogen-containing solvent. Preferred solvents are benzonitrile, N-methyl-2-pyrrolidinone, dimethylformamide, and 1,4-dicyanobutane. Other solvents which may be utilized include dimethyl sulfoxide and sulfolane.

When a mixture of cuprous bromide and lithium cyanide is used, the lithium cyanide is used in approximately stoichiometric amounts based on the reactant chlorobenzene and the cuprous bromide is used in an amount of from about 0.1 to about 2.0 equivalent based on the chlorobenzene, preferably from about 0.5 to about 1.0. Temperatures and reaction times are as above.

The examples which follow depict the conduct of the process according to this invention, primarily showing the production of 4-cyano-3-nitrobenzotrifluoride ($R_1$ is trifluoromethyl, $R_2$ is hydrogen) as a representative compound. However, similar conditions, metallic bromides, and the like may be used for production of other compounds of this type such as those mentioned above.

EXAMPLE 1

Preparation of 4-Cyano-3-Nitrobenzotrifluoride

In a flask were placed 1.13 grams (g) (5.0 mmol) 4-chloro-3-nitrobenzotrifluoride, 0.4478 g (5.0 mmol) cuprous cyanide, 0.4342 g (5.0 mmol) lithium bromide and 10 milliliters (ml) N-methyl-2-pyrrolidinone, under a nitrogen blanket. The reaction mixture was then heated to a temperature of 175° C. and reaction was continued at a range of 172°–178° C. over a period of 24 hours. At the end of that run, the heat source was removed and the reaction mixture cooled. Product was recovered by washing with water, 3M HCl, diethyl ether, again with 3M HCl, and again with ether. The ether extract was dried over magnesium sulfate, filtered and the solvent stripped, yielding 0.875 g (81% of theoretical yield) of an amber, somewhat tarry looking oil, which was identified by gas chromatographic analysis as the desired product.

The gas chromatographic analysis indicated that the final mixture contained 62 area % of the desired product, 18 area % of the starting material and 4 area % 2-nitro-4-trifluoromethylphenol by-product.

EXAMPLES 2-8

The process as described above in Example 1 was carried out using different solvents, or in the absence of a solvent. In general, the reactions were run with one equivalent each of 4-chloro-3-nitrobenzotrifluoride, cuprous cyanide and lithium bromide. The amount of solvent was 1 ml/mmol starting chlorobenzene in Examples 2 and 6, and 2 ml/mmol in the remaining examples. The results in these experiments are tabulated in the following Table 1. Product mixture composition was determined by gas chromatography. The distribution of the product mixture is shown as between the desired cyano compound, the starting material and the by-product 2-nitro-4-trifluoromethylphenol.

TABLE 1

| | | | | Product Mixture, Area % | | |
|---|---|---|---|---|---|---|
| Ex. | Solvent | Temp., °C. | Time, hours | Cyano compound | Starting material | Phenol |
| 2 | dimethylformamide | 165–165 | 5 | 70 | 24 | 1 |
| 3* | CN(CH$_2$)$_4$CN | 172–178 | 3 | 88 | 4 | 1 |
| 4 | none | 147–152 | 5 | trace | 99 | — |
| 5** | none | 172–178 | 30 | 96 | 4 | — |
| 6*** | benzonitrile | 195–200 | 6 | 91 | 5 | trace |
| 7 | dimethyl sulfoxide | 160–180 | 8 | 44 | 25 | 2 |

TABLE 1-continued

| | | | | Product Mixture, Area % | | |
|---|---|---|---|---|---|---|
| Ex. | Solvent | Temp., °C. | Time, hours | Cyano compound | Starting material | Phenol |
| 8 | sulfolane | 190–200 | 7 | 91 | 5 | 1 |

*Worked up after 6 hours to give 49.5% corrected yield of cyano.
**Worked up to give 15% yield of cyano compound; reaction run in a heel of the cyano compound.
***Worked up to give 79.2% corrected yield of cyano compound.

COMPARATIVE EXAMPLE 1

This example illustrates the poor results obtained by the use of lithium chloride instead of lithium bromide.

In a flask were placed 1.13 g (5.0 mmol) 4-chloro-3-nitrobenzotrifluoride, 0.448 g (5.0 mmol) cuprous cyanide and 0.21195 g (5.0 mmol) lithium chloride. There was then added 10 ml benzonitrile. The reaction was conducted under a nitrogen blanket at a temperature of 182°–185° C. for 6 hours. Gas chromatographic analysis of the product mixture at this point showed 72 area % unreacted starting material and only 27 area % of the desired cyano compound. For comparison, Example 6, conducted at slightly higher temperature over the same period using lithium bromide rather than lithium chloride, produced 91 area % of the desired compound and only 5 area % unreacted starting material.

EXAMPLES 9-14

These examples illustrate production of 4-cyano-3-nitrobenzotrifluoride using the metal bromides as catalyst. The reactions were carried out as in Examples 2–8 using 1 equivalent of cuprous cyanide per equivalent of starting chlorobenzene and 2 ml benzonitrile solvent per mmol chlorobenzene. Table 2 below shows the temperatures, reaction times and equivalent amounts of the various metal bromides. The product mixture is again given in terms of gas chromatographic analysis by area % in terms of the desired cyano compound, the starting material and by-product 4-bromo-3-nitrobenzotrifluoride ("bromo compound").

TABLE 2

| | (Solvent -- Benzonitrile) | | | | | | |
|---|---|---|---|---|---|---|---|
| | | | | | Product Mixture, Area % | | |
| Ex. | Bromide | Equivalents | Temp. °C. | Time hrs. | Cyano compound | Starting Material | Bromo compound |
| 9 | NaBr | 1.0 | 190–193 | 6 | 65* | 2 | trace |
| 10 | NaBr (C$_6$H$_5$)$_4$PBr | 1.0 0.1 | 188–192 | 3** | 75 | 22 | 2 |
| 11 | NaBr CuBr$_2$ | 1.0 0.1 | 191–193 | 2** | 63 | 34 | 1 |
| 12 | MgBr$_2$ etherate | 0.5 | 182–184 | 6 | 85 | 12 | 2 |
| 13 | CaBr$_2$ | 0.5 | 190–193 | 7 | 84 | 12 | 3 |
| 14 | ZnBr$_2$ | 0.5 | 189–193 | 7 | 77 | 12 | trace*** |

*m-Nitrobenzotrifluoride also detected.
**Decomposition occurred on further heating.
***2,4,6,-Triphenyl-s-triazine also detected.

COMPARATIVE EXAMPLE 2

This example illustrates the conduct of the reaction using cuprous bromide instead of lithium bromide.

The process was run similarly to those described above for Examples 9-14. Cuprous bromide was used in an amount of 1.0 equivalent per equivalent of the starting chlorobenzene. The solvent was benzonitrile, reaction temperature was 180°-194° C. and the time of the reaction was 3 hours.

Gas chromatographic analysis of the product mixture at the end of this time indicated approximately 52 area % of the desired benzonitrile, about 16 area % of starting material and only a trace amount of the bromo compound. There was also detected the presence of m-nitrobenzotrifluoride.

EXAMPLE 15

This example demonstrates the use of a combination of lithium cyanide and cuprous bromide for this reaction.

There were placed in a flask 2.26 g (10 mmol) 4-chloro-3-nitrobenzotrifluoride, 2.869 g (10 mmol) cuprous bromide and 20 ml of a 0.5 molar solution of lithium cyanide in dimethylformamide which contained 1.0 equivalent of lithium cyanide with respect to the starting chlorobenzene.

The reaction temperature was maintained at 158°-159° C.; the time of the run was 6 hours. At the end of this time, the product mixture was analyzed by gas chromatography. It showed the following:

| | |
|---|---|
| cyano compound | 81 area % |
| starting chlorobenzene | 12 area % |
| dimethylamino-substituted benzene | 2 area % |
| bromo-substituted benzene | trace |
| hydroxy-substituted benzene | not detected |

EXAMPLE 16

This example illustrates the production of 2-nitrobenzonitrile by the process of this invention.

This reaction was conducted similarly to those reported above, using a mixture of cuprous cyanide and lithium bromide. The ratios of reactants were (by equivalents) 2-chloronitrobenzene:cuprous cyanide:lithium bromide=1:1.1:0.3. The solvent was benzonitrile. The reaction was run for one hour at a temperature of 169°-190° C. and for five additional hours at a temperature of 190°-192° C. At the end of a total six-hour period gas chromatographic analysis showed the product to contain 82 area % of the desired product 2-nitrobenzonitrile, 11 area % of starting material and 3 area % of the bromo-substituted compound.

Additional examples of this type were conducted, using in one case nitrobenzene as the solvent, and in other cases without a solvent. In general, the processes produced the desired product in a predominating amount, although the reaction was slower and lower temperatures of about 150°-165° C. were necessary to avoid undue by-product formation.

What is claimed is:

1. A process for the production of an ortho-nitrobenzonitrile by reaction of the corresponding ortho-nitrochlorobenzene with:
    (a) cuprous cyanide and a metal bromide selected from alkali metal bromides, alkaline earth metal bromides, and zinc bromide, or
    (b) lithium cyanide and cuprous bromide.

2. A process according to claim 1 conducted in the presence of a solvent selected from benzonitrile, N-methyl-2-pyrrolidinone, N,N-dimethylformamide, 1,4-dicyanobutane, sulfolane or dimethyl sulfoxide.

3. A process according to claim 1 in which the cuprous or lithium cyanide is used in a stoichiometric amount with respect to the ortho-nitrochlorobenzene.

4. A process according to claim 1 in which the ratio of bromide compound to ortho-nitrochlorobenzene is from 0.1 to 2.0 equivalent per equivalent.

5. A process according to claim 4 in which the ratio of bromide compound to ortho-nitrochlorobenzene is from about 0.5 to about 1.0 equivalent per equivalent.

6. A process according to claim 1 in which the temperature is from about 100° to about 200° C.

7. A process according to claim 1 in which the ortho-nitrobenzonitrile has the formula

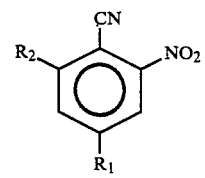

wherein $R_1$ and $R_2$ are independently hydrogen or an electron-withdrawing group.

8. A formula according to claim 7 in which $R_1$ and $R_2$ are independently hydrogen, nitro, $C_1$-$C_4$ alkylsulfonyl, halo-($C_1$-$C_4$ alkyl)sulfonyl, cyano, carboxyl or halomethyl.

9. In a process for production of ortho-nitrobenzonitriles by reaction of an ortho-nitrochlorobenzene with cuprous cyanide and an inorganic salt, the improvement comprising utilizing as the inorganic salt an alkali metal bromide, an alkaline earth metal bromide, or zinc bromide.

* * * * *